Nov. 1, 1960 O. O. DUNHAM Plant Pat. 1,978
CHRYSANTHEMUM PLANT
Filed July 27, 1959
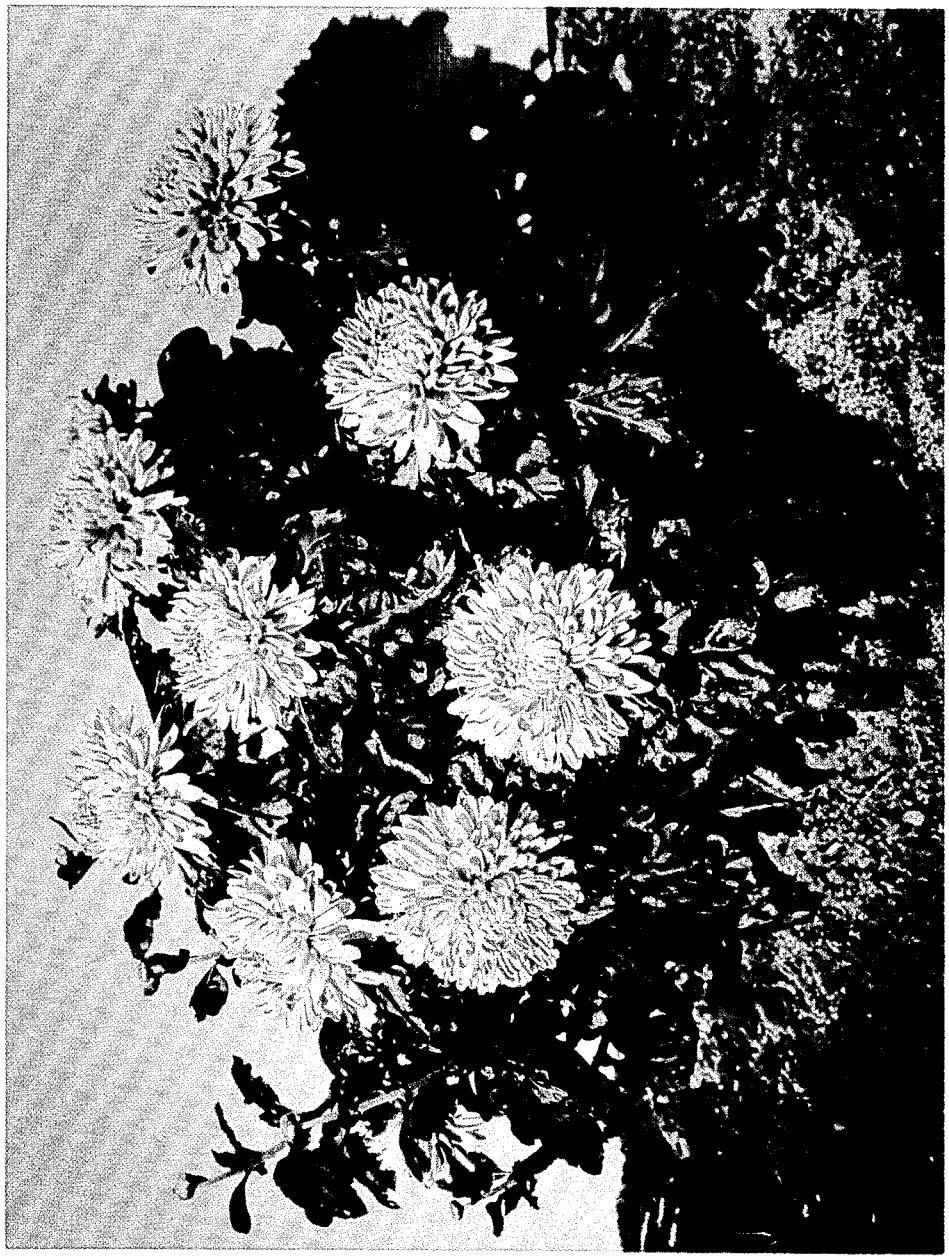
Inventor
O. O. Dunham
by
Robb & Robb
attorneys United States Patent Office Plant Pat. 1,978
Patented Nov. 1, 1960

1,978

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,941

1 Claim. (Cl. 47—60)

My present invention comprises a new and distinct variety of chrysanthemum plant which is the result of crossing a variety of my own introduction identified as "Her Ladyship" (unpatented) and the unpatented variety "His Lordship," also an introduction of mine.

The object of my invention has been to produce a new variety of chrysanthemum of the *indicum* type which will be earlier than most varieties and whose foliage will be an improvement over either of the parents with a color of bloom somewhat like both parents.

In order to produce a number of varieties of better characteristics along the lines indicated before, I have conducted an intensive program of careful selection and cross-breeding so as to produce a number of varieties of chrysanthemum having earliness of blooming and continuous blooming as important characteristics.

The result of the specific hybridization initially mentioned is my present new and distinct variety of chrysanthemum plant, characterized by the moderate orange yellow to strong orange yellow color of its blooms, the very double arrangement of its petals, vigorous, branching, more compact habit of growth, improved foliage, the large size and hardiness of its blooms, and the early, continuous and long blooming period.

More specifically, the blooms of my new variety undergo quite a marked change from the bud form to the final fully blown flower varying from a vivid yellow to strong orange to strong orange yellow (Nickerson Color Fan produced by Munsell Color Co.).

As grown in the vicinity of Niles, Michigan, under uniform culture, plants of my new variety attain an average height of 15 to 18 inches.

In some respects my new variety bears a closer resemblance to its parent "His Lordship" as to color, than to its other parent "Her Ladyship," my new variety differs from both of its parents and some other known varieties in many respects.

When comparing the color of the blooms of my new variety with the color of the blooms of the variety "His Lordship," it is to be noted that the color of the blooms of the latter are more red where the color of the blooms of my new variety are more orange to orange yellow. The petal arrangement in the variety "Her Ladyship" is very tight, the variety hereof is very double and includes innumerable petals thereon.

Under conditions of culture in the region of Niles, Michigan, my new variety produces blooms which average about five inches in diameter (disbudded), borne in clusters and with medium strong stems.

When grown in the region of Niles, Michigan, blooms of my new variety commence about mid-September and are profuse and continuous in nature until the killing frost.

The earliness of my new variety is a product of the combination of the parents. In this instance the pollen parent is "Her Ladyship," whereas the seed parent is "His Lordship." The pollen parent "Her Ladyship" flowers later and the seed parent "His Lordship" earlier and thus the flowers of the seedling hereof are mid-way between the said parents.

An important improvement of my new variety over either of the parents is the foliage which is very abundant having a dark green upper side with glossy texture.

The hardiness of the flower of my new variety and its general form may be said to derive from the pollen parent "Her Ladyship" and constitutes an improvement over both parents.

My new variety has been asexually reproduced by cuttings, in the vicinity of Niles, Michigan.

My new variety has been found to retain its distinctive characteristics through successive asexual reproductions.

The accompanying drawing, forming a part hereof, shows a typical plant of my variety of chrysanthemum.

The following is a detailed description of my new variety of chrysanthemum plant, the color references being to the Nickerson Color Fan produced by Munsell Color Company:

Parentage: Seedling.
*Seed parent.*—"His Lordship" (unpatented).
*Pollen parent.*—"Her Ladyship" (unpatented).

Classification: Botanic—*Chrysanthemum indicum.* This variety is numbered 56161 for purposes of identification.

*Flower*

Blooming habit: Blooms profusely from mid-September until killing frost producing a profuse succession of blooms for a long season, the observations in this particular instance having been made at Niles, Michigan in September.

Bud:
*Size.*—Large.
*Form.*—Short with flat top. Not affected by wet weather. Not affected by hot weather.
*Color.*—When petals begin to unfurl—Munsell Hue 5Y 8/12 vivid yellow washed with 5Y R 7/11 strong orange. When half blown: inside of petals—Munsell Hue 5Y 8/12 vivid yellow washed with 5YR 7/11 strong orange; reverse of petals—Munsell Hue 5Y 9/9 brilliant yellow washed with 7.5YR 8/8 moderate orange yellow.
*Sepals.*—Of no consequence.
*Peduncle.*—Long.
*Aspect.*—Rough.
*Color.*—Medium green.
*Strength.*—Stiff; erect.
*Opening.*—Bud opens well; somewhat affected by adverse conditions.

Bloom:
*Size.*—Large. Average size when fully expanded—5 inches (disbudded).
*Borne.*—In clusters—irregular.
*Stems.*—Medium; strong.
*Form.*—Flat. Permanence—retains its form to the end.
*Petalage.*—Very double. Number of petals under normal conditions—innumerable.
*Color.*—Center of flower—between 5YR 7/11 and 5YR 6/11 Munsell Hue 5YR. Outer petals—between 7.5YR 8/8 and 7.5YR 7/11 Munsell Hue 7.5YR. Base of petals (singlet)—between 5YR 7/11 and 5YR 6/11 Munsell Hue 5YR. Inside of petals—between 5YR 7/11 and 5YR 6/11 Munsell Hue 5YR. Reverse of petals—between 7.5YR 8/8 and 7.5YR 7/11 Munsell Hue 7.5YR. General tonality from a distance—between 7.5YR 8/8 and 7.5YR 7/11 Munsell Hue 7.5YR.
*Discoloration.*—First week—retains the same color. Second week—retains much the same color. Third week—retains much the same color.

Petals:

*Texture.*—Thin. Bleaching in hot weather. Affected by fungus infection in wet weather.

*Appearance.*—Velvety inside—satiny outside.

*Form.*—Pointed.

*Arrangement.*—Imbricated.

*Persistance.*—Hang on and dry.

*Lastingness.*—On the plant—very long. As cut flower—long.

Genital organs:

*Stamens, anthers.*—Small; few.

*Color.*—Yellow.

*Arrangement.*—Regular around styles.

*Stamens, filaments.*—Short.

*Color.*—White.

*Styles.*—Columnar.

*Length.*—Short.

*Stigmas.*—White.

*Ovaries.*—All enclosed in calyx.

Fruit: Variety is fertile with its own pollen.

*Form.*—Oblong shaped.

*Aspect.*—Rough.

*Color at maturity.*—Brownish grey.

*Plant*

Form: Bush.

Growth: Vigorous, dwarf, branching, compact.

Foliage:

*Size.*—Large.

*Quantity.*—Abundant.

*Color.*—New foliage: upper side—normal green; under side—light green. Old foliage: upper side—dark green; underside—dark green.

*Shape.*—Three lobed.

*Texture.*—Upper side—glossy; flat. Under side—velvety. Ribs and veins—ordinary.

*Edge.*—Smooth.

*Leaf stem.*—Green in color. Under side—smooth.

*Stipules.*—Short.

*Disease resistance.*—Under certain conditions susceptible to mildew.

I claim:

A new and distinct variety of chrysanthemum plant substantially as herein disclosed, characterized as to novelty by the moderate orange yellow to strong orange yellow color of its blooms, the very double arrangement of its petals, vigorous, branching, more compact habit of growth, improved foliage, large size and hardiness of its blooms, and the early, continuous, and long blooming period.

No references cited.